United States Patent
Budge et al.

(10) Patent No.: US 7,464,319 B2
(45) Date of Patent: Dec. 9, 2008

(54) FORWARD ERROR CORRECTION WITH CODEWORD CROSS-INTERLEAVING AND KEY-BASED PACKET COMPRESSION

(75) Inventors: Scott Budge, Logan, UT (US); Yong Zhang, Bellevue, WA (US)

(73) Assignee: Utah State University, Logan, UT (US)

( * ) Notice: Subject to any disclaimer, the term of this patent is extended or adjusted under 35 U.S.C. 154(b) by 1132 days.

(21) Appl. No.: 10/639,847

(22) Filed: Aug. 13, 2003

(65) Prior Publication Data

US 2004/0243913 A1 Dec. 2, 2004

Related U.S. Application Data

(60) Provisional application No. 60/466,288, filed on Apr. 29, 2003.

(51) Int. Cl.
*H03M 13/00* (2006.01)

(52) U.S. Cl. .................. 714/762; 714/788; 714/756

(58) Field of Classification Search ......... 714/755–756, 714/776, 782, 784, 788, 762
See application file for complete search history.

(56) References Cited

U.S. PATENT DOCUMENTS 6,571,369 B1 * 5/2003 Li ........................... 714/792
6,868,514 B2 * 3/2005 Kubo et al. ................ 714/755

* cited by examiner

*Primary Examiner*—Guy J Lamarre
(74) *Attorney, Agent, or Firm*—Workman Nydegger

(57) ABSTRACT

An encoder encodes each of a plurality of data fragments into an encoded packet comprising a plurality of codewords, each codeword comprising a set of data bytes from the data fragment and at least one error-correction byte derived from the set of data bytes. A plurality of cross-interleavers each receive as input one of the plurality of codewords of the encoded packet, after which a concatenator concatenates a plurality of interleaved codewords output by the plurality of cross-interleavers into an interleaved packet to be sent over a network.

42 Claims, 16 Drawing Sheets

FORWARD ERROR CORRECTION WITH CODEWORD CROSS-INTERLEAVING AND KEY-BASED PACKET COMPRESSION

CROSS-REFERENCE TO RELATED APPLICATIONS

This application is related to and claims the benefit of U.S. Provisional Application No. 60/466,288, filed Apr. 29, 2003, for "Forward Error Correction in a Multimedia Data Stream," with inventor Yong Zhang, which application is incorporated herein by reference in its entirety.

TECHNICAL FIELD

The present invention relates generally to the field of electronic communication. More specifically, the present invention relates to techniques for reducing latency in electronic communication.

BACKGROUND OF THE INVENTION

Several methods exist for correcting network transmission errors. One is commonly referred to as Automatic Repeat Request (ARQ). Standard communication protocols, such as the Transmission Control Protocol (TCP), use ARQ to correct transmission errors by asking a source host to retransmit lost packets. Unfortunately, ARQ causes significant delay in transmitting real-time multimedia data, which can result in dropped video frames, audio degradation, etc. This is one reason that TCP is often not suitable for multimedia applications.

Another method is Forward Error Correction (FEC). FEC coding (also called channel coding) adds redundant data, called parity bytes, into a data stream prior to transmission. Using this redundancy, the FEC algorithm can detect and even correct the errors caused by corruption of the data channel without having to request retransmission of a packet.

FEC coding is often used in conjunction with the User Datagram Protocol (UDP), which, in contrast to TCP, provides a way for applications to send raw IP datagrams without having to establish a connection. UDP supports quick connections and transportation, but does not guarantee that a UDP datagram will ever reach its final destination. Internet phone applications and real-time video conferencing systems often use UDP because they can tolerate a small fraction of packet loss or out-of-order reception.

FEC coding, alone, is generally not sufficient to eliminate transmission errors, since many such errors result from the loss of whole network packets rather than the corruption of individual bits or bytes. Packets can be lost for many reasons, such as a failure in a switch or end-site device buffer. Encoding redundant data within a packet does not help restore the packet if it is completely lost.

Accordingly, techniques have been developed for recovering whole packets. One approach is interleave each network packet with data from a series of FEC-encoded packets. Hence, if a network packet is lost, then only a single byte from each of the FEC-encoded packets is lost. The lost bytes can then be recovered using redundant information in adjacent packets.

Unfortunately, such conventional approaches to correcting whole packet loss introduce considerable latency, which can also be a significant problem in real-time multimedia transmission.

DETAILED DESCRIPTION OF PREFERRED EMBODIMENTS

Figure 1:
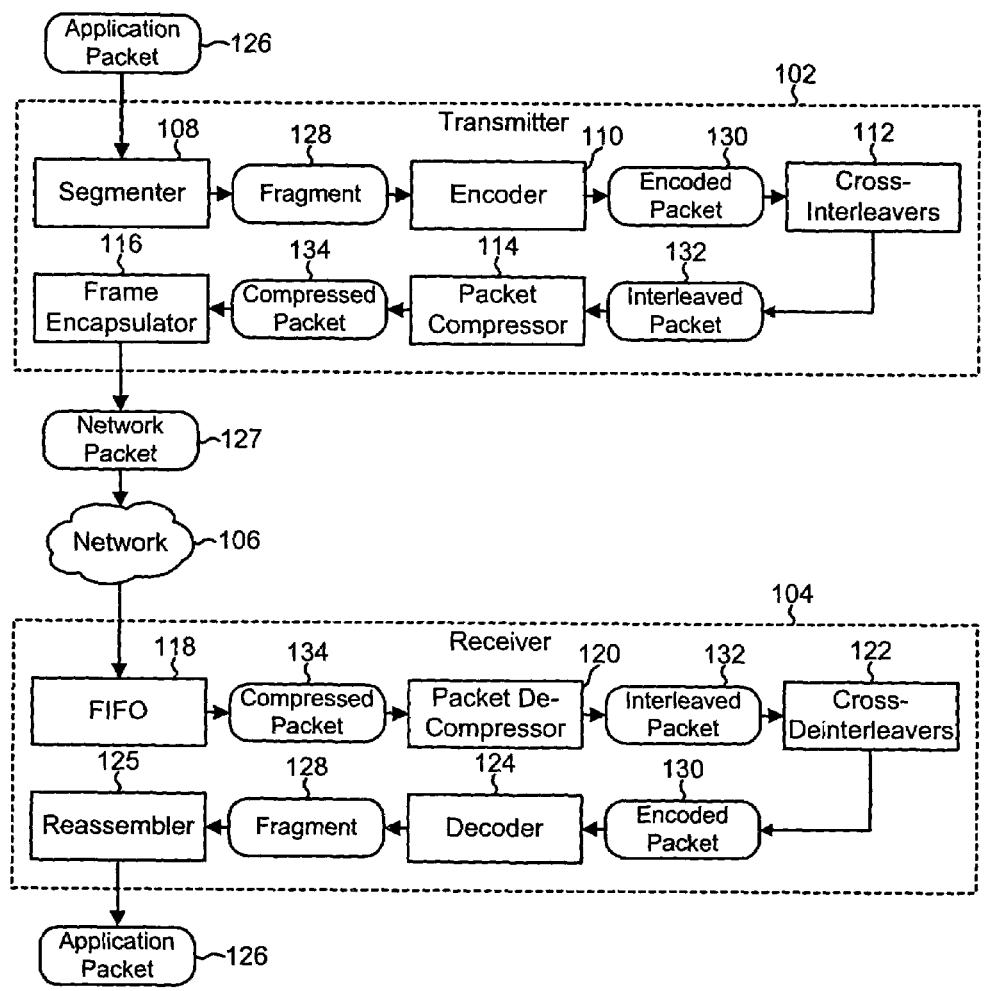
FIG. 1 is a block diagram of a communication system.

Reference is now made to the figures in which like reference numerals refer to like elements. For clarity, the first digit of a reference numeral indicates the figure number in which the corresponding element is first used.

In the following description, numerous specific details of programming, software modules, user selections, network transactions, database queries, database structures, etc., are provided for a thorough understanding of the embodiments of the invention. However, those skilled in the art will recognize that the invention can be practiced without one or more of the specific details, or with other methods, components, materials, etc.

In some cases, well-known structures, materials, or operations are not shown or described in detail in order to avoid obscuring aspects of the invention. Furthermore, the described features, structures, or characteristics may be combined in any suitable manner in one or more embodiments.

FIG. 1 is a high-level block diagram of a communication system 100 according to an embodiment of the invention. As illustrated, the system 100 includes a transmitter 102 and a receiver 104, each of which may be implemented within the context of a personal computer (PC), video-conferencing system, teleconferencing system, multi-endpoint communication system, Internet telephone device, interactive television (ITV) system, or other communication system or device.

In one embodiment, the transmitter 102 is connected to the receiver 104 by a packet-switched network 106, one particular example of which is the Internet. Communication over the network 106 is accomplished using standard protocols, such as the User Datagram Protocol (UDP) and Internet Protocol (IP), although other protocols may be used within the scope of the invention.

As illustrated, the transmitter 102 may include a number of components or modules, such as a segmenter 108, an encoder 110, a plurality of cross-interleavers 112, a packet compressor 114, and a frame encapsulator 116. Likewise, the receiver 104 may include a FIFO 118, a packet decompressor 120, a plurality of cross-deinterleavers 122, a decoder 124, and a reassembler 125. Each of the aforementioned components or modules may be implemented using any suitable combination of hardware and/or software. Furthermore, the transmitter 102 and the receiver 104 may include other standard components not illustrated but known to those of skill in the art.

As described in greater detail below, the transmitter 102 obtains an application packet 126 to be sent to the receiver 104 through the network 106. The application packet 126 may include, for example, video data and/or audio data. However, the application packet 126 may also include other types of data and meta data, such as program code, text, etc.

Typically, the application packet 126 will be too large to be sent over the network 106 within a single network packet 127. This is particularly true in the case of video packets. Accordingly, in one embodiment, the segmenter 108 divides the application packets 126 into a plurality of uniform-length fragments 128. The size of the fragments 128 impacts latency, as will be described in greater detail below.

The encoder 110 encodes each fragment 128 into an encoded packet 130 containing error-correction data, commonly referred to as "parity" bytes. The parity bytes include redundant data that allow the receiver 104 to detect as well as correct transmission errors. The use of parity bytes to correct transmission errors is commonly referred to as Forward Error Correction (FEC). This is opposed to Automatic Repeat Request (ARQ), which is used by TCP to ask a source host to retransmit lost packets.

As previously noted, many transmission errors are the result of whole packet loss rather than corruption of individual bits or bytes. Accordingly, the plurality of cross-interleavers 112 interleave the data of a series of encoded packets 130 into a number of interleaved packets 132. This is done so that the loss of one network packet 127 (which encapsulates an interleaved packet 132) will only result in the loss of a single byte of several encoded packets 130. The bytes can later be recovered using error-correction techniques.

As explained more fully below, each of the cross-interleavers 112 interleaves a different piece or segment of an encoded packet 130 in parallel with the other cross-interleavers 112. The resulting interleaved data from each cross-interleaver 112 is then concatenated to produce an interleaved packet 132.

In one embodiment, a separate cross-interleaver 112 is provided for each piece or segment of the encoded packet 130. For example, if a packet contains 312 bytes and the segment size is 12 bytes, then 26 cross-interleavers are used, each of which is configured to receive a different 12-byte segment (or "codeword") of an encoded packet 130. The novel process of using separate cross-interleavers 112 to interleave the codewords of an encoded packet 130 is referred to herein as "codeword cross-interleaving."

The interleaving process will typically result in the addition of padding or zero bytes to the interleaved packet 132. Accordingly, using techniques described hereafter, the packet compressor 114 compresses each interleaved packet 132 to remove the padding. The resulting compressed packet 134 is then provided to the frame encapsulator 116, where it is encapsulated within a network packet 127 and sent to the receiver 104 via the network 106.

Within the receiver 104, the FIFO 118 receives each network packet 127 in turn, performing packet reordering if necessary, and provides the included compressed packets 134 to the packet decompressor 120. Thereafter, the packet decompressor 120 reinserts any padding bytes into the compressed packets 134 that were removed by the packet compressor 114, restoring the original interleaved packets 132.

In one embodiment, the plurality of cross-deinterleavers 122 deinterleave the data from the interleaved packets 132 to recover the encoded packets 130, as described in greater detail hereafter. The decoder 124 then removes the parity bytes from the encoded packets 130 and/or corrects any transmission errors. The resulting fragments 128 may then be reassembled by the reassembler 125 to restore the application packet 126.

The foregoing description is a high-level overview of a process that will be described more fully in the following specification. Those of skill in the art will recognize that the above-described components or modules may be combined in any number of configurations. Furthermore, the processes performed by each of the described components may occur in a different order from that which is illustrated without departing from the spirit and scope of the invention.

Figure 2:
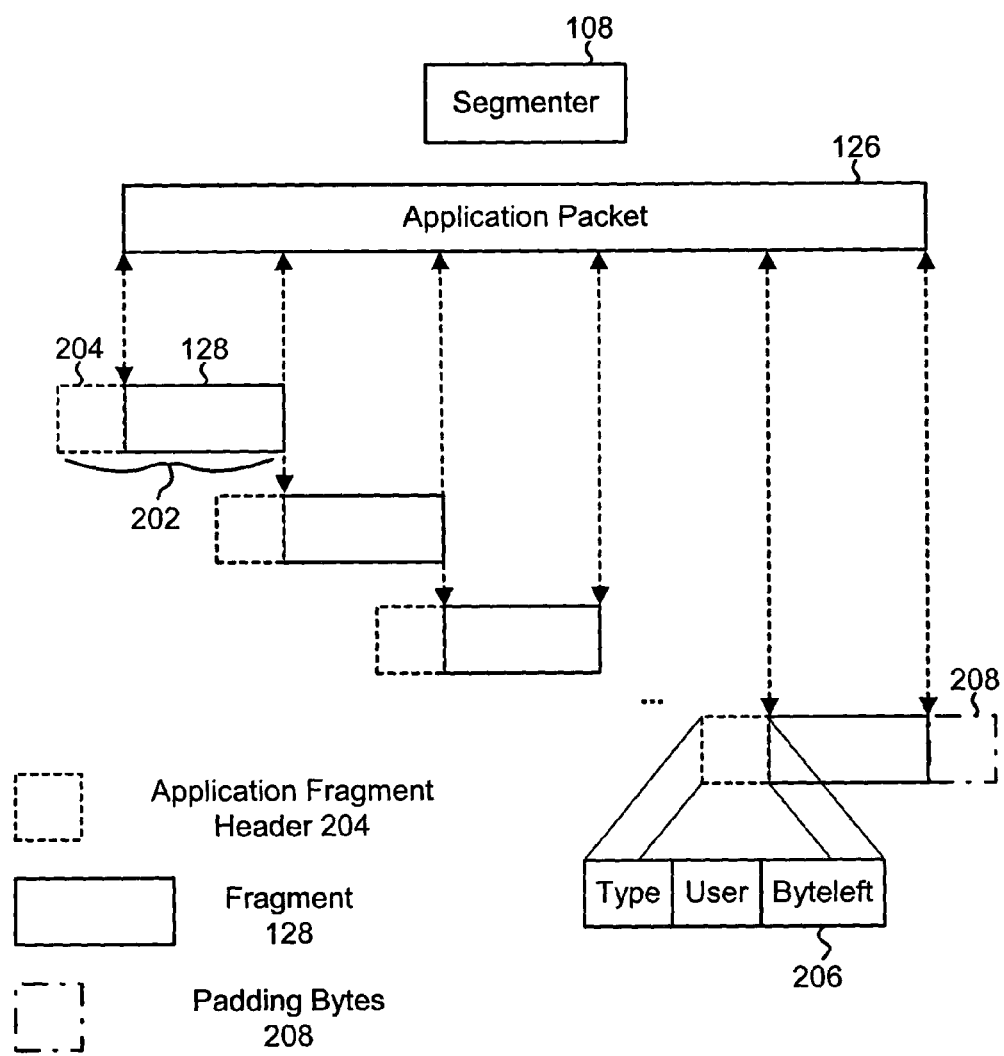
FIG. 2 is a block diagram of a segmenting process.

FIG. 2 illustrates additional details of the segmenter 108. As noted above, each application packet 126 is segmented into several small fragments 128 of uniform length. In the example embodiment described hereafter, the length of a fragment is 278 bytes. The length is chosen by considering the latency caused by the cross-interleavers 112 for a particular network bandwidth (i.e., 128 kbits/second). In other networks 106 and configurations, different lengths would be chosen.

In one embodiment, a UDP fragment 202 is created by adding an application fragment header 204 onto a fragment 128. Of course, other protocols could be used besides UDP, and the invention should not be construed as being limited in that respect. In other embodiments, the fragment 128, itself, may be passed directly to the encoder 110. The application fragment header 204 includes, in the depicted embodiment, a Byteleft field 206, which indicates how many bytes follow the current UDP fragment 202 to complete the application packet 126. The application fragment header 204 may also include various other fields known to those of skill in the art, such as a Type field and a User Field. Other fields could be provided within the scope of the invention.

Assume the length of a video application packet is 8000 bytes. The Byteleft field 206 for the first fragment 128 is 8000−278=7722, which means that there are 7722 bytes after this fragment 128. The Byteleft field 206 for the second fragment 128 is 7722−286=7436. In one implementation, padding (e.g., zero bytes) 208 is added to the last UDP fragment 202 as necessary to keep the length uniform. In the illustrated embodiment, the length of the application fragment header 204 is 8 bytes, resulting in a length of a UDP fragment 202 of 286 bytes. Those of skill in the art will recognize that these numerical values are provided herein by way of example and not of limitation.

Figure 3:
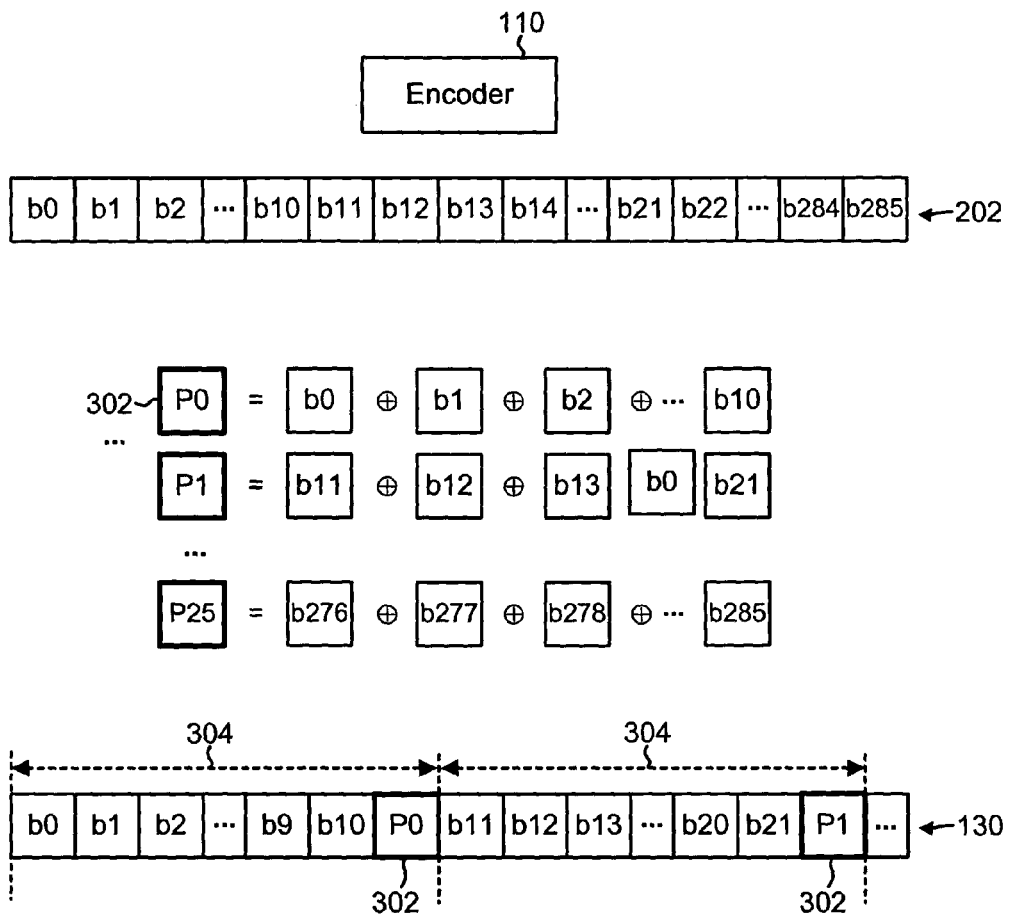
FIG. 3 is a block diagram of an encoding process.

FIG. 3 provides additional details of the encoder 110. In one implementation, the encoder 110 uses a basic error correction algorithm, such as XOR coding, which simplifies real-time processing. Other known coding systems may be used within the scope of the invention, such as Reed-Solomon coding or BCH coding, although these methods are more complex and require higher computational overhead.

To illustrate the XOR encoding process, assume that [b0, b1, b2, . . . , b10, b11, b12, . . . , b284, b285] is a UDP fragment 202. In one embodiment, a parity byte 302 is inserted after every 11 data bytes to create a 12 byte codeword 304, resulting in an encoded packet length of 312 bytes. There are 312/12=26 codewords 304 in one encoded packet 130. Any number of parity bytes 302 may be added to a codeword 304 within the scope of the invention.

In the depicted embodiment, the encoded packet 130 is given by [b0, b1, b2, . . . b9, b10, P0, b11, b12, . . . b21, P1, . . . b276, b277, . . . , b285, P25], where:

P0=⊕b0 b1⊕ . . . b10

P1=b11⊕b12⊕ . . . b21

P25=⊕b276⊕277 ⊕ . . . b285

⊕ being the XOR operation.

As shown above, the parity byte 302 is defined by XORing the 11 data bytes of the codeword 304. If a byte in a codeword 304 is lost, it can be recovered by XORing the other 11 bytes. For example, b2=b0⊕b1⊕b3⊕ . . . ⊕b10⊕b11⊕P0.

In the depicted embodiment, the codewords 304 are of uniform length. However, in alternative embodiments, certain codewords 304 may be shorter than others in order to provide increased error-correcting ability. For example, the first two codewords 304 may only include 6 bytes, while the remaining codewords are 12 bytes each. The shorter codewords 304 may be used, for example, to store a header area of the application packet 126, which may be more critical than other data.

Figure 4:
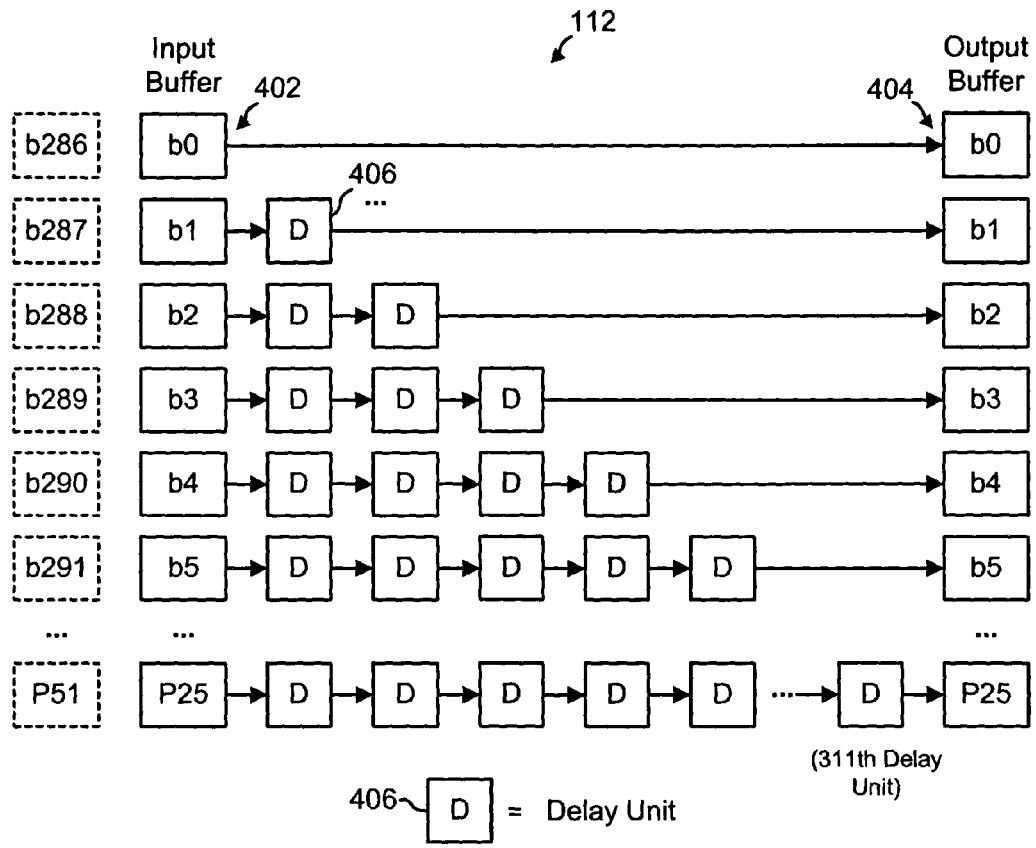
FIG. 4 is a block diagram of a conventional cross-interleaver.
Figure 4:
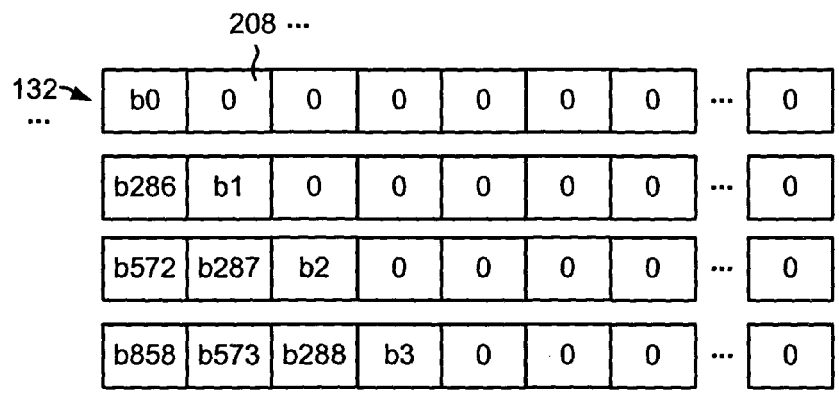

FIG. 4 illustrates a conventional cross-interleaving process. As noted above, interleaving is desirable because it distributes the data of an encoded packet 130 among a series of network packets 127. Thus, if a network packet 127 is lost, for example, due to the failure of a switch, only a single byte of a number of encoded packets 130 is lost. These bytes can be recovered using redundant information in adjacent encoded packets 130.

As illustrated, a standard cross-interleaver 112 includes an input buffer 402 and an output buffer 404. The input buffer 402 receives an encoded packet 130, e.g. [b0, b1, b2, . . . b9, b10, P0, b11, b12, . . . b21, P1, . . . b276, b277, . . . , b285, P25]. Depending on the position of a particular byte of the encoded packet 130 within the input buffer 402, the byte will pass through a different number of delay units 406 before reaching the output buffer 404. For example, byte "b0" will pass immediately to the output buffer 404, while byte "b1" will encounter one delay unit 406, byte "b2" will encounter two delay units 406, and so on, increasing to a maximum delay of 311. Each time an encoded packet 130 is placed into the input buffer 402, the cross-interleaver 112 pushes some bytes out of the delay units 406 into the output buffer 404.

FIG. 4 illustrates the first four interleaved packets 132 sent to the output buffer 404 based on the example data. For instance, the first 312-byte interleaved packet 132 consists of byte "b0" followed by 311 padding bytes 208 (e.g., zeroes), which occur because the corresponding data bytes are still within the delay units 406. Likewise, the second 312-byte interleaved packet 132 consists of bytes "b286" and "b1" followed by 310 padding bytes 208.

One of ordinary skill in the art will recognize that the padding bytes 208 introduce latency. For example, the cross-interleaver 112 will need to interleave 312 encoded packets 130 before generating an interleaved packet 132 that contains no padding. This is undesirable in many respects and may be particularly detrimental to real-time multimedia transmissions.

Figure 5:
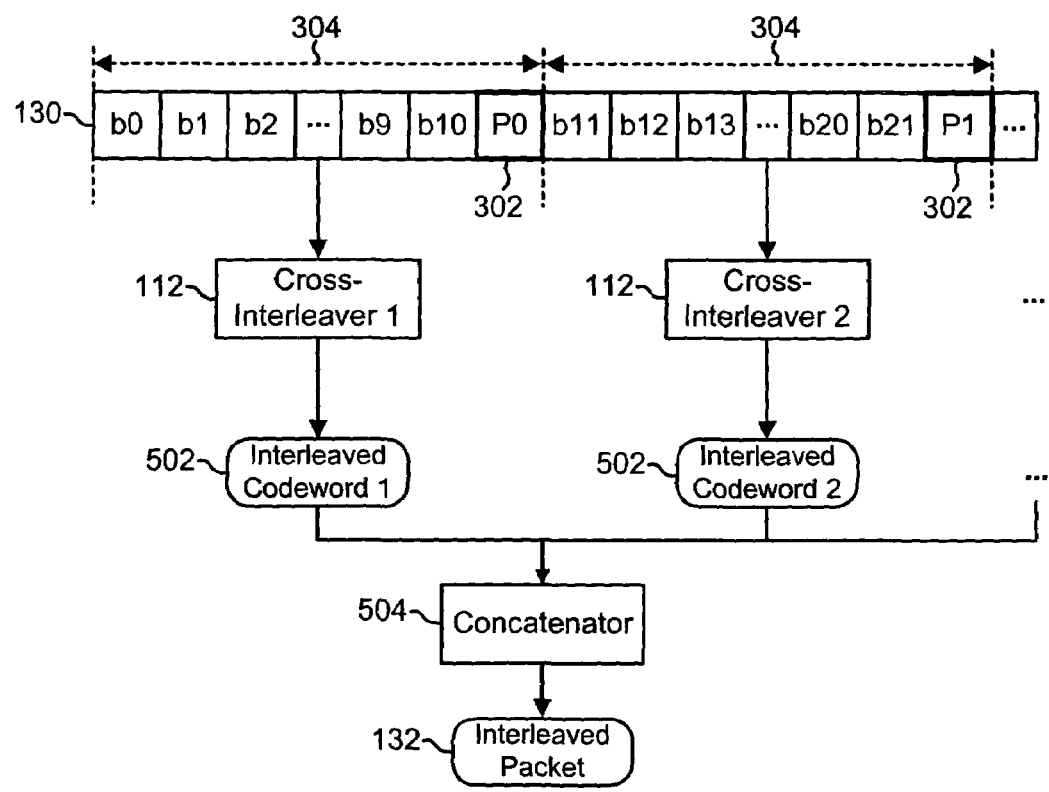
FIG. 5 is a block diagram of a plurality of cross-interleavers for interleaving different segments of an encoded packet.

Accordingly, as shown in FIG. 5, one embodiment of the present invention uses a plurality of cross-interleavers 112, one for each codeword 304 of the encoded packet 130. Accordingly, in the example embodiment, twenty-six (26) cross-interleavers 112 would be used.

Each of the cross-interleavers 112 produces an interleaved codeword 502 in its respective output buffer 404. In one embodiment, a concatenator 504 concatenates the interleaved codewords 502 from the plurality of cross-interleavers 112 to create the interleaved packet 132.

Figure 6:
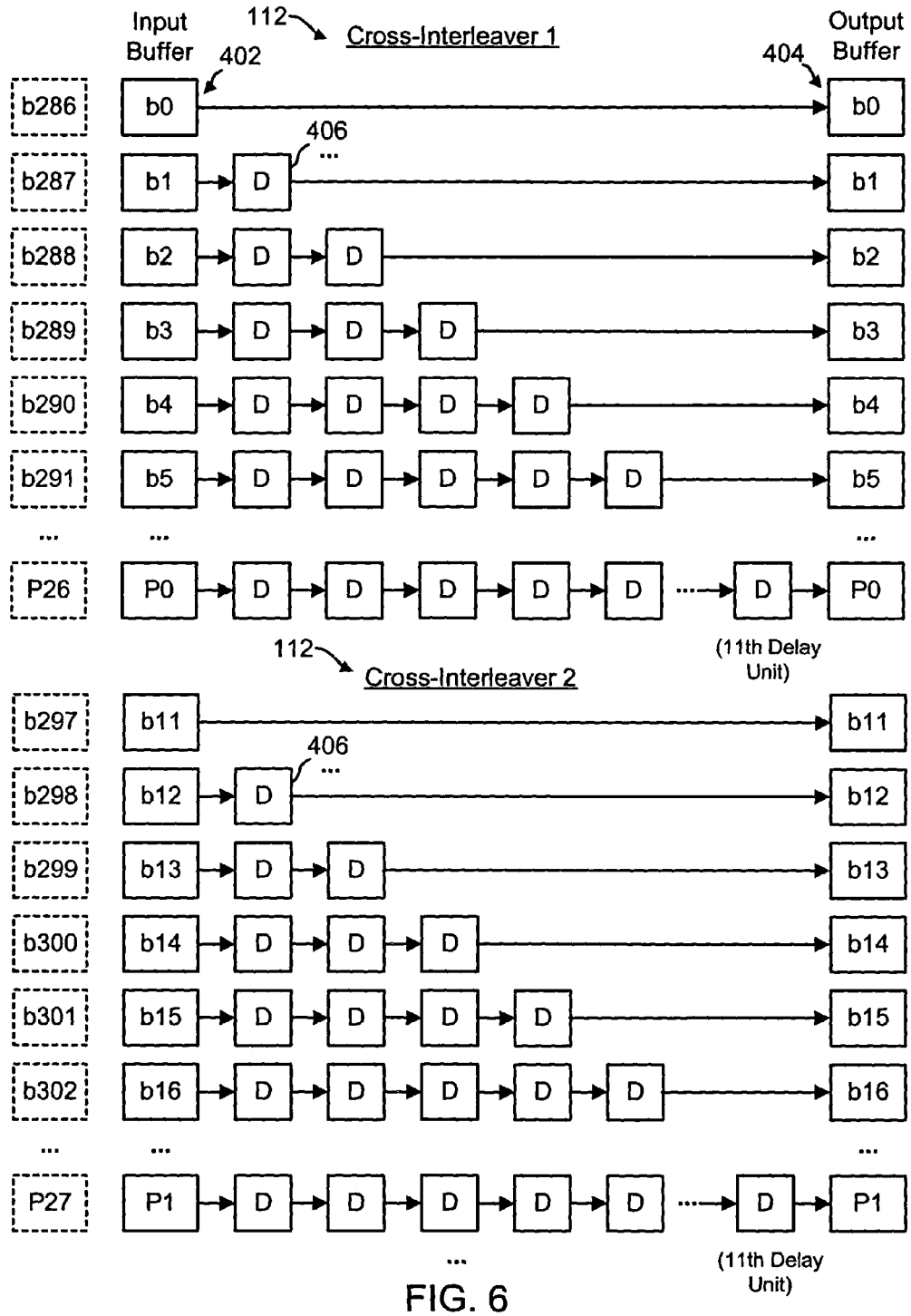
FIG. 6 is a detailed block diagram of two cross-interleavers.

FIG. 6 is a detailed block diagram of two of the cross-interleavers 112, each of which includes a set of delay units 406. However, unlike the conventional cross-interleaver 112 of FIG. 5, the number of delay units 406 for a particular byte increases from zero to the size of a codeword 304 (e.g., 12 in the example embodiment) rather than the size of an encoded packet 130.

In certain embodiments, a single module or device could be used to implement the plurality of cross-interleavers 112. Hence, references herein to "separate" or "different" cross-interleavers 112 may refer to a single module or device that implements the functionality of multiple cross-interleavers 112. However, as will be apparent from a comparison of FIG. 6 with FIG. 4, the structure of the delay units 406 within a combination of twenty-six, 12-byte cross-interleavers 112 is substantially different from that of a unitary 312-byte cross-interleaver.

Figure 7:
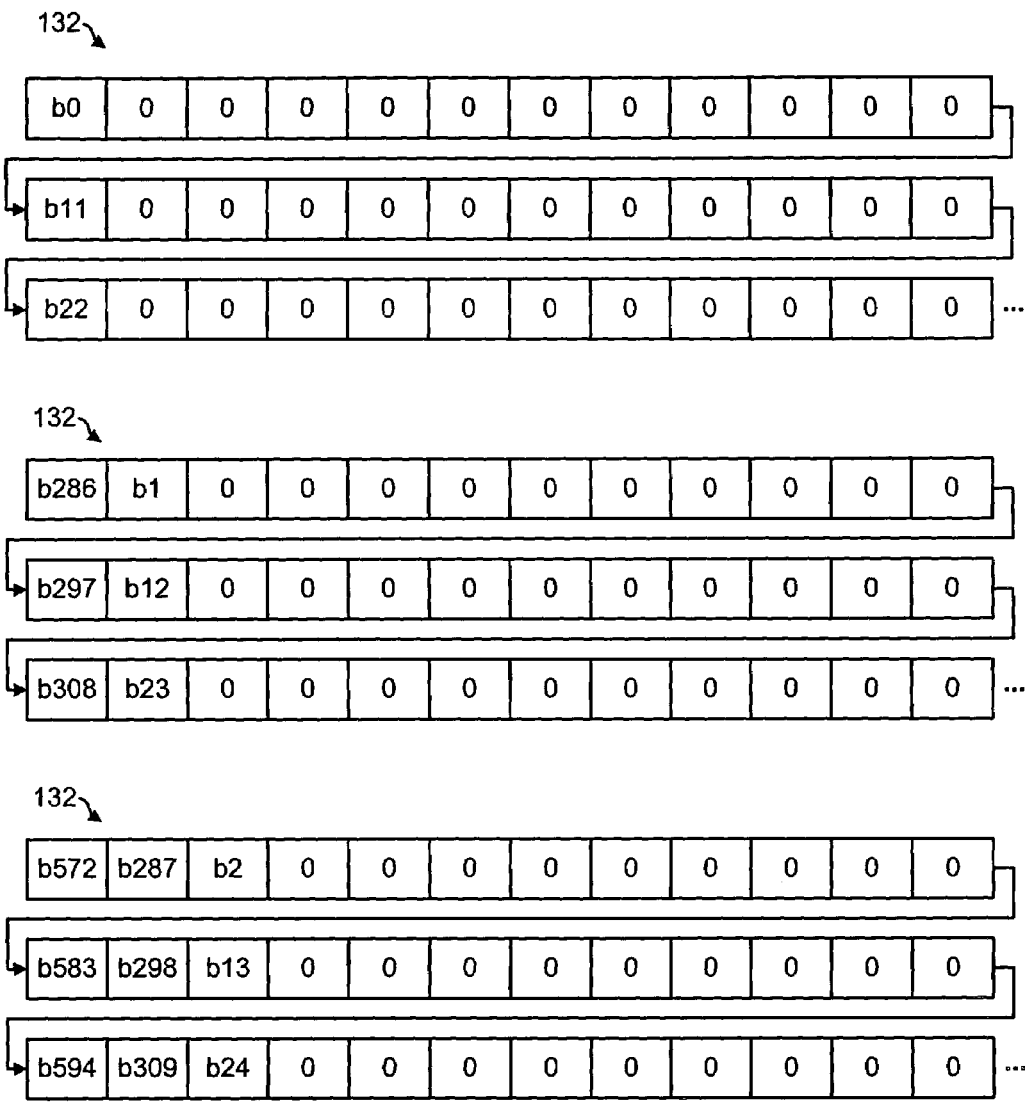
FIG. 7 is a block diagram of exemplary interleaved packets produced by a plurality of cross-interleavers.

FIG. 7 illustrates portions of the first three interleaved packets 132 that would be produced in the example embodiment. For instance, the first interleaved packet 132 would contain byte "b0" followed by 11 zeroes, byte "b11" followed by 11 more zeros, byte "b22" followed by another 11 zeroes, and so on. Thus, the first interleaved packet 132 of FIG. 7 would contains 26 bytes of valid data, as opposed to only one byte of valid data from the unitary cross-interleaver 112 of FIG. 5. Similarly, the second interleaved packet 132 of FIG. 7 would contain 52 bytes of valid data, while the second interleaved packet 132 of the standard cross-interleaver 112 would contain only 2 bytes of valid data.

Based on the foregoing, the plurality of cross-interleavers 112 will only need to interleave 12 encoded packets 130 before producing an interleaved packet 132 that contains no padding. By contrast, the single cross-interleaver 112 would need to process 312 encoded packets 130 before achieving the same result.

As noted above, the relative sizes of the codeword 304 and the fragment 128 impact latency. For example, the latency caused by the cross-interleavers 112 in the example embodiment is given by:

Latency=12 packets (312+12+28) bytes/packet=4224 bytes where:

312 is the length of the interleaved packet, 12 is the length of the frame head, and 28 is the length of the UDP/IP layer header.

Assume, for instance, that the network bandwidth is 128 kbits/s. The latency would thus be calculated to be 4224×8/128000=0.264 seconds. Table 1 shows the latency caused by the cross-interleavers 112 for various codeword and fragment lengths.

TABLE 1

| Fragment Length | 252 | 278 | 289 | 300 | 304 | 316 | 330 |
|---|---|---|---|---|---|---|---|
| Codeword Length | 11 | 12 | 12 | 12 | 13 | 13 | 14 |
| Latency (secs.) | 0.2445 | 0.264 | 0.273 | 0.282 | 0.2835 | 0.2932 | 0.303 |

The foregoing shows that the longer the codeword and fragment lengths are, the smaller the bandwidth overhead, the weaker the error correction ability, and the higher the latency. Thus, one may choose the optimal codeword and fragment lengths to minimize the latency for the particular network 106 for a desired error protection level, network bandwidth, or both.

Figure 8:
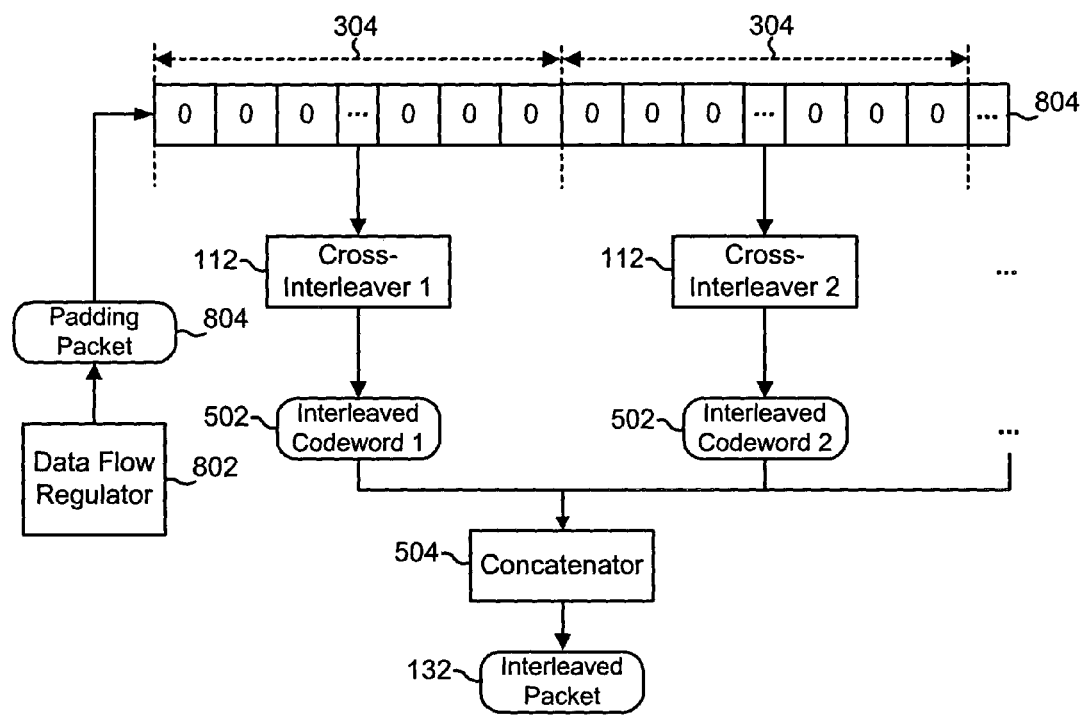
FIG. 8 is a block diagram of a data flow regulator in combination with a plurality of cross-interleavers.

Referring to FIG. 8, the present invention also mitigates another source of latency—when the network speed is greater than the application packet data generation rate. After all of the encoded packets 130 of one application packet 126 are put into the cross-interleavers 112, some bytes of the application packet 126 are still stored in the delay units 406. Typically, the cross-interleavers 112 would have to wait until the next new application packet 126 is generated, which can push those bytes into the output buffer 404.

In one embodiment, when an encoded packet 130 is not yet available to be input into the cross-interleavers 112, a data flow regulator 802 inputs a padding packet 804 (having 312 padding bytes 208 in the exemplary embodiment) into the cross-interleavers 112 to push out the delayed bytes instead of waiting for the next new application packet 126 to do so.

If the network speed is much greater than the application packet generation rate, the data flow regulator 802 will input eleven padding packets 804 into the cross-interleavers 112. If the network speed is only a little greater than the application data generation rate, fewer than eleven padding packets 804 are input into the cross-interleavers 112. Of course, if the network speed is equal to the application data generation rate, the new application packet 126 will be ready in time. Hence, no padding packets 804 are needed.

Figure 9:
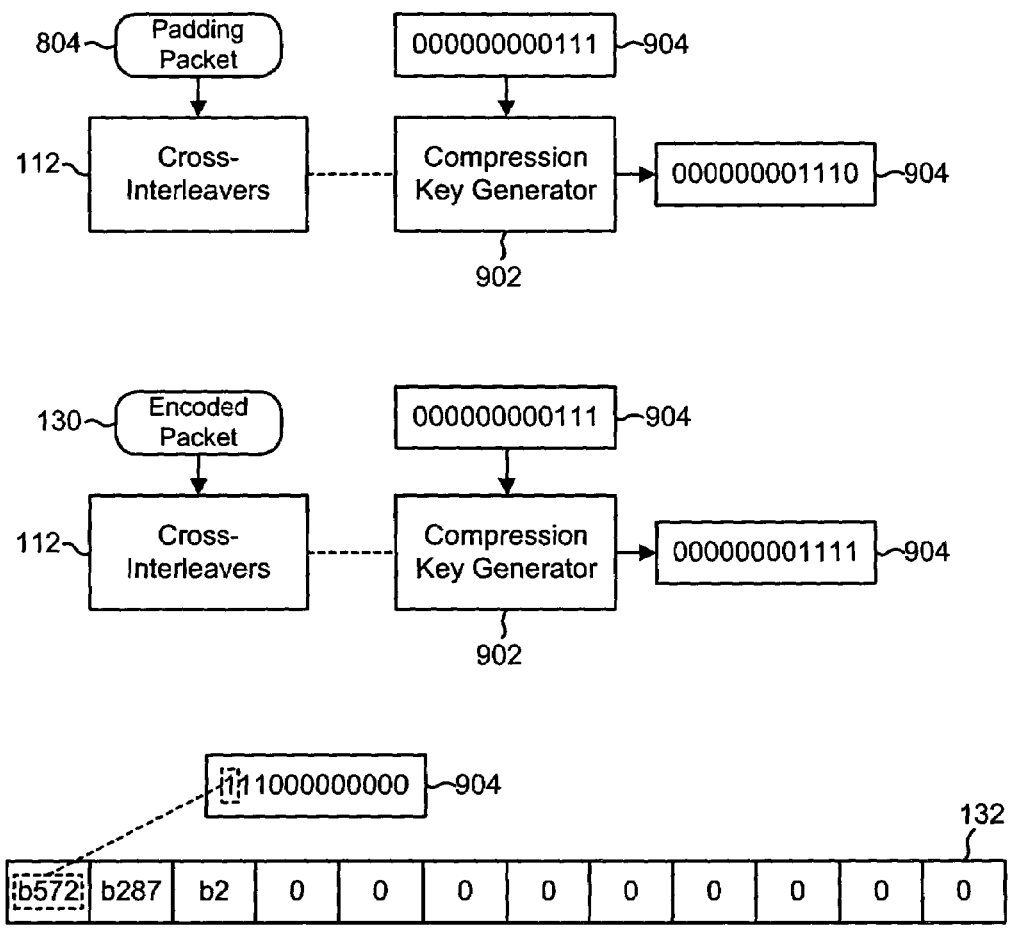
FIG. 9 is a block diagram of a process for creating compression keys.

Referring to FIG. 9, as explained above, the addition of padding by the data flow regulator 802 and the cross-interleavers 112 is a source of latency. Accordingly, in one implementation, the padding is removed from the interleaved packets 132 prior to transmission. To accomplish this, a compression key generator 902 creates a compression key 904 indicating which bytes of each interleaved codeword 502 of an interleaved packet 132 contain valid data and which bytes contain padding.

The compression key 904 may be embodied as a "bitmap" of an interleaved codeword 502, where a "1" in the compression key 904 indicates that a corresponding byte of the interleaved codeword 502 contains valid data, while a "0" indicates that the corresponding byte contains padding. Since each of the interleaved codewords 502 of an interleaved packet 132 contain the same pattern of valid data and padding, the compression key 904 applies to the entire interleaved packet 132.

In one embodiment, the compression key 904 for an interleaved packet 132 is initially set to zero. Thereafter, each time a padding packet 804 is input into the cross-interleavers 112, the compression key generator 902 shifts the compression key 904 left by one bit, resulting in a zero being stored in the first bit of the compression key 904. If, however, an encoded packet 130 is input into the cross-interleavers 112, the compression key generator 902 both left-shifts the compression key 904 and increments the compression key 904 (adds 1). Those of skill in the art will recognize that the compression key 904 could be generated in other ways without departing from the spirit and scope of the invention.

Figure 10:
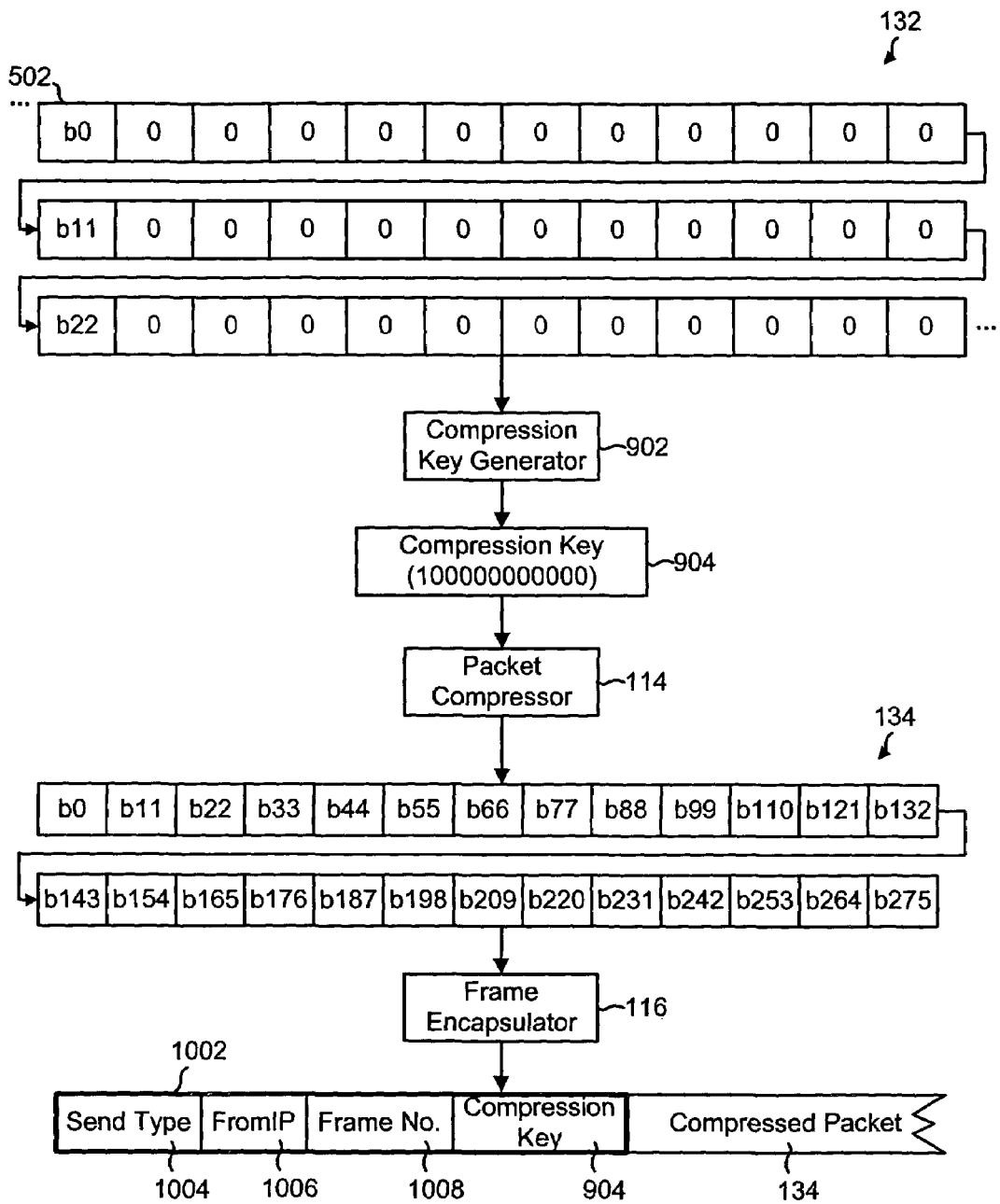
FIG. 10 is a block diagram of a process for removing padding from an interleaved packet using a compression key.

As shown in FIG. 10, the packet compressor 114 removes the padding from the interleaved packet 132. In the example embodiment, the compression key 904 of "100000000000" indicates that only the first byte of each interleaved codeword 502 contains valid data, while the remaining 11 bytes contain padding. Accordingly, the packet compressor 114 removes the padding from each interleaved codeword 502, resulting in a compressed packet 134 that is 26 bytes long as opposed to 312 bytes long. Note that where the compression key 904 is created as described in the preceding paragraph, the compression key 904 would actually be "000000000001." To create the depicted compression key 904, a process of right-shifting and inserting leading 1's could be done in an alternative embodiment.

In one embodiment, the frame encapsulator 116 generates network packets 127 by adding a network packet header 1002 to each compressed packet 134. The network packet header 1002 may include various data fields, including a SendType field 1004, a FromIP field 1006, a FrameNumber 1008 field, as well as the compression key 904 for the compressed packet 134.

The SendType field 1004 defines how the packet is to be sent. In one implementation, there are three kinds of packets 127: broadcast, unicast, and multicast. The FromIP field 1006 defines the Internet Protocol (IP) address of the computer that generated the network packet 127. The FrameNumber field 1008 is an order number used to locate lost network packets 127 and reorder out-of-order packets 127. The FrameNumber field 1008 is incremented with each new network packet 127.

Figure 11:
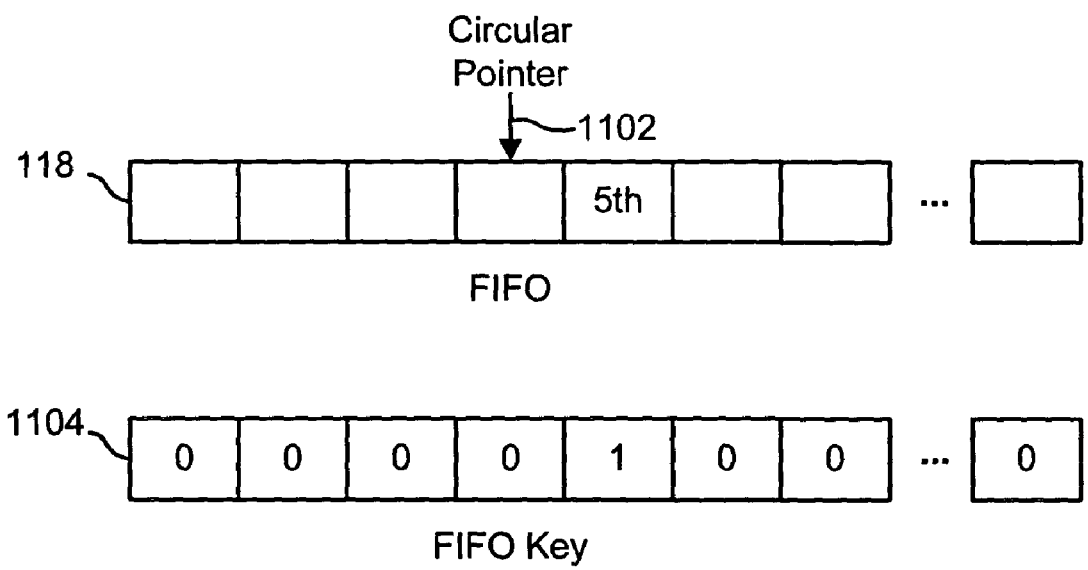
FIG. 11 is a block diagram of a FIFO.

FIG. 11 illustrates details of the FIFO 118 within the receiver 104. In one embodiment, the FIFO 118 receives each network packet 127 in turn, some of which may be out of order based on the FrameNumber field 1008. The FIFO 118 includes a circular pointer 1102 which points to a location for the next expected network packet 127 in the FIFO 118. At the same time, another buffer, called a FIFO Key 1104, is used to indicate whether the units in the FIFO 118 are occupied or not.

When all of the network packets 127 arrive at the receiver 104 in order, they are simply put into FIFO 118 and returned to the packet decompressor 120 with the network packet header 1002 removed. The circular pointer 1102 jumps once each time. Under this condition, there is no additional latency.

However, suppose the first three packets 127 arrive in order and the 5th packet 127 arrives before the 4th packet 127. As illustrated, the first three buffer units are empty because the first three packets 127 have been moved to the packet decompressor 120. The expected 4th packet does not arrive, so the circular pointer 1102 still points to the 4th buffer unit. After the 5th packet 127 arrives and is stored in the corresponding buffer unit, the fifth byte in the FIFO Key 1104 is "1," which means that the fifth buffer unit in the FIFO 118 is occupied. After the 4th packet 127 arrives, the next expected packet is the 6$^{th}$ packet 127, the 5th packet 127 having arrived earlier. The circular pointer points to the 6th buffer unit. Thereafter, the 4th and 5th packets 127 in the FIFO 118 are returned to the packet decompressor 120 in order. In this way, the FIFO 118 is used to reorder the out-of-order network packets 127.

The FIFO 118 may also be used to detect lost network packets 127. Suppose the nth packet 127 is lost. The subsequent packets 127 keep arriving and are put into the FIFO 118 until the (n+x)th packet 127 is received, after which the FIFO 118 returns a 312-byte padding packet 804 to the packet decompressor 120 which replaces the lost (nth) packet 127. The bigger "x" is, the better the reorder ability, and the higher the latency, since latency=x bytes/packet. For example, if x=5, the latency is 1390 bytes. Thus, if a network packet is out-of-order by 6 or more, it is beyond the reorder ability of the illustrated FIFO 118. The FIFO 118 will be convinced that the packet 127 is lost and error correction techniques will be used to recover the packet 127.

Figure 12:
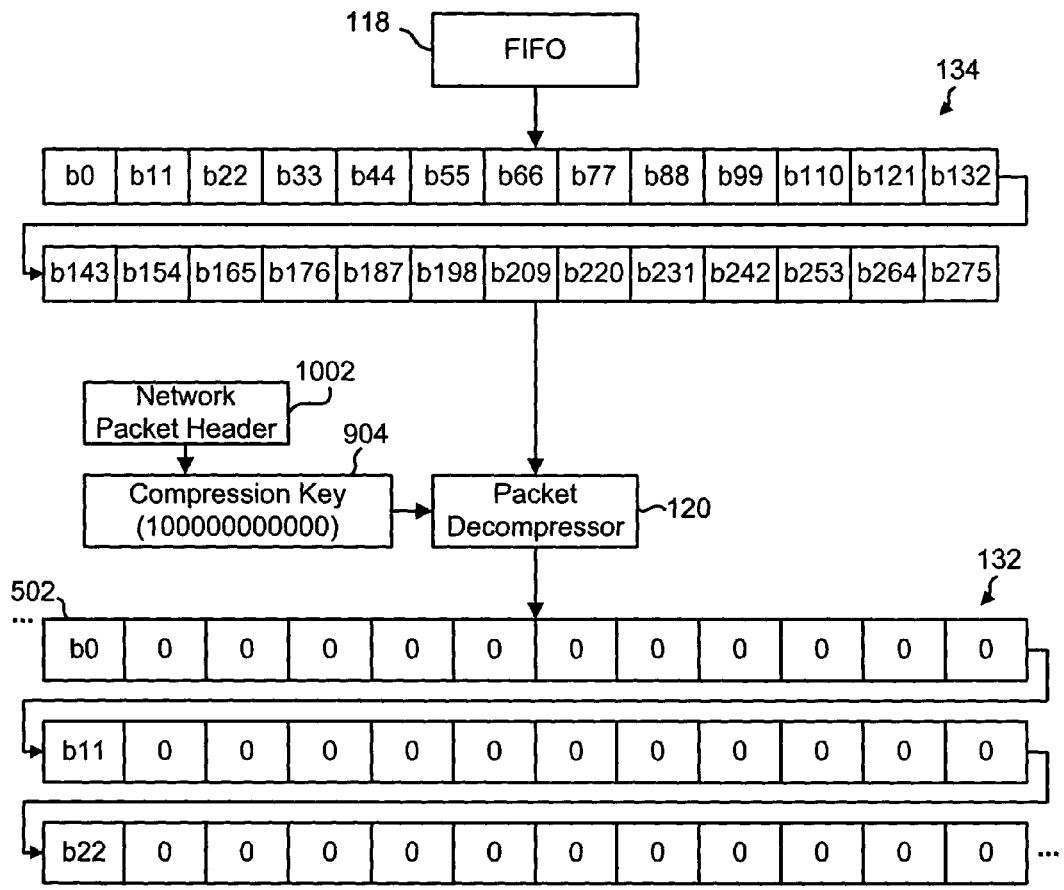
FIG. 12 is a block diagram of a process for reinserting removed padding using a compression key received with a packet.

Referring to FIG. 12, the packet decompressor 120 uses the compression key 904 from the network packet header 1002 to reinsert the padding removed by the packet compressor 114. As noted above, the compression key 904 maps the valid data and padding within the interleaved codewords 502 of an interleaved packet 132. Thus, for each interleaved codeword 502, a "1" in the compression key 904 indicated that a data byte should be copied from the compressed packet 134 to a new (uncompressed) interleaved codeword 502. Thus, a compression key 904 of "1000000000" indicates that a byte should be copied from the compressed packet 134 into the first byte of each interleaved codeword 502 of the interleaved packet 132. By contrast, a "0" within the compression key 904 indicates that a padding (zero) byte 208 is to be inserted into corresponding locations of each interleaved codeword 502.

Figure 13:
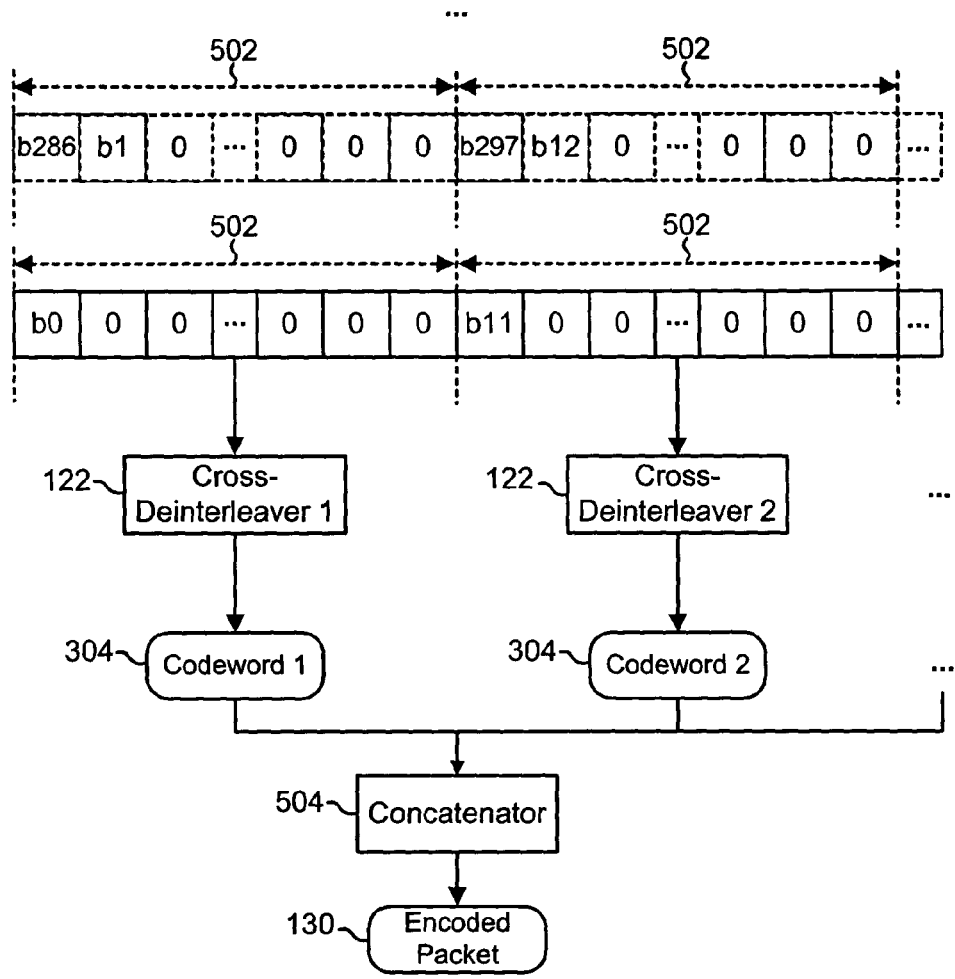
FIG. 13 is a block diagram of multiple cross-deinterleavers for deinterleaving segments of an interleaved packet.

Referring to FIG. 13, the interleaved codewords 502 of an interleaved packet 132 are then input into different cross-deinterleavers 122, which produce deinterleaved codewords 304 (referred to herein simply as "codewords") in their respective output buffers 404. The concatenator 504 may then concatenate the codewords 304 to recover one of the original encoded packets 130.

Figure 14:
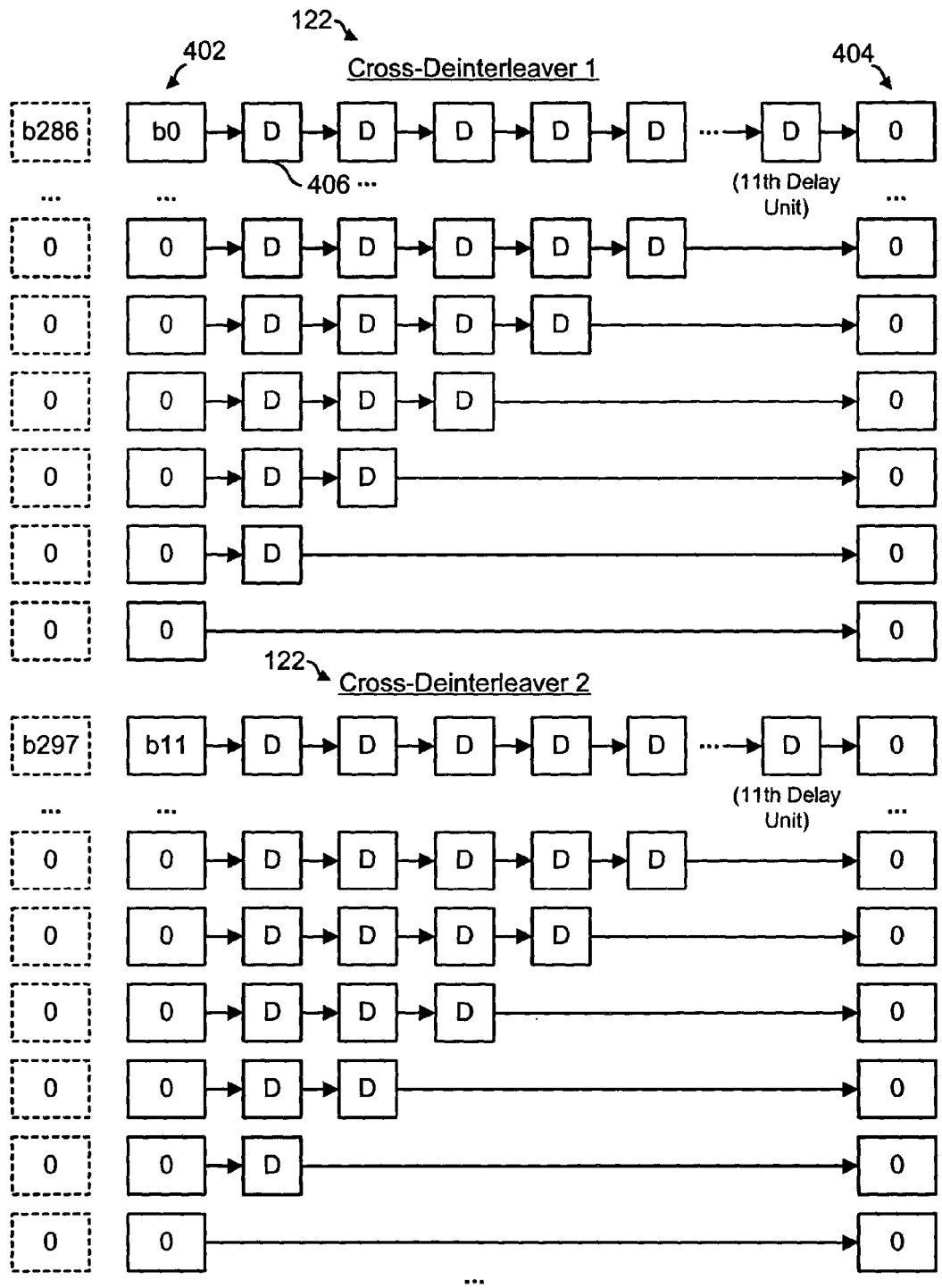
FIG. 14 is a detailed block diagram of two cross-deinterleavers.

As illustrated in FIG. 14, the structure of the cross-deinterleavers 122 is similar to that of the cross-interleavers 112, but inverted. For example, the first byte of each codeword will pass through 11 delay units 406 in the example embodiment, with the number of delay units 406 decreasing until the last byte proceeds without delay to the output buffer 404. Those of skill in the art will recognize that, in the example embodiment, 12 interleaved packets 132 would need to be input into the plurality of cross-deinterleavers 122 before the first encoded packet 130 is ready. Inputting the 13$^{th}$ interleaved packet 132 would result in the 2$^{nd}$ encoded packet 130, and so on.

Figure 15:
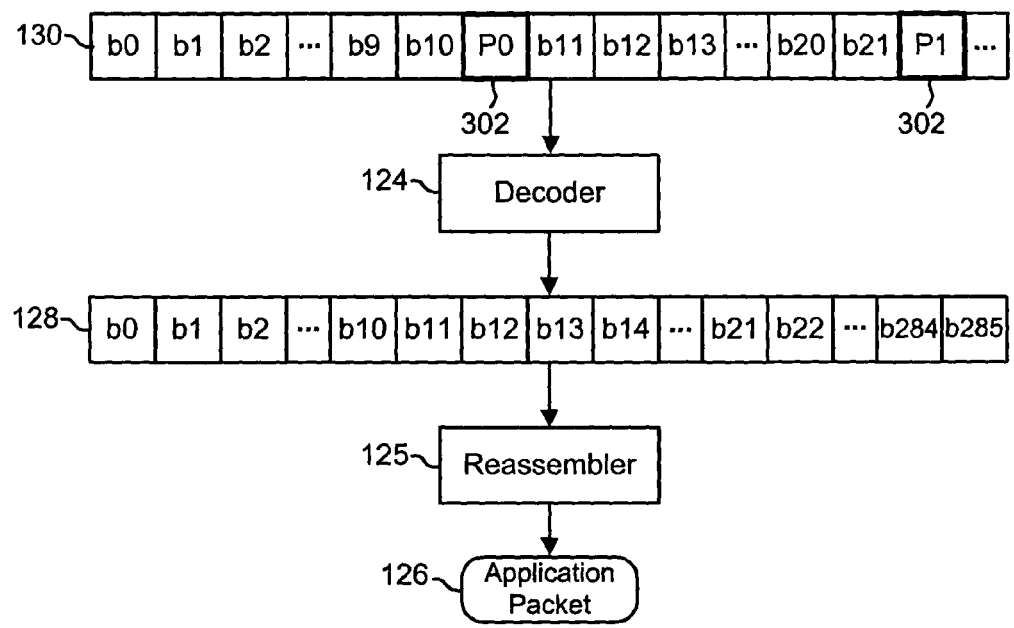
FIG. 15 is a block diagram of a decoding process.

Referring to FIG. 15, assuming there were no transmission errors, the decoder 124 simply removes the parity bytes 302 from the encoded packet 130 to recover a fragment 128 of the application packet 126. Once all of the fragments 128 of the application packet 126 have been decoded, the reassembler 125 may reassemble the fragments 128 into the original application packet 126.

Figure 16:
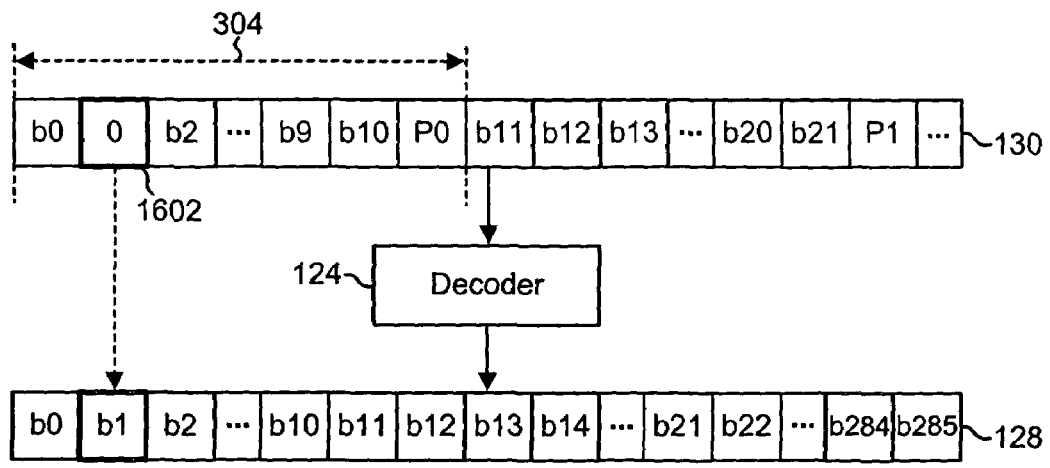
FIG. 16 is a block diagram of an error-correction process.

If, as shown in FIG. 16, a byte 1602 in a codeword 304 was lost due to the loss of a network packet 127, the byte 1602 may be recovered. In one embodiment, the decoder 124 is in communication with the FIFO 118 to determine which bytes 1602 in which encoded packets 130 were lost.

In the depicted embodiment, a lost byte 1602 in a codeword 304 is recovered from the other bytes of the codeword 304. For example, the byte "b1" may be recovered by XORing the other bytes, i.e., b1=b0⊕b2⊕ . . . P0. Of course, with FEC-coding techniques, such as Reed-Solomon coding, different recovery methods would be used.

Although the present invention has been described in the context of a fully functional data processing system and/or network, those of skill in the art will appreciate that the mechanism of the present invention is capable of being distributed in the form of a computer-usable medium of instructions in a variety of forms, and that the teachings of the present invention apply equally regardless of the particular type of signal-bearing medium used to actually carry out the distribution.

While specific embodiments and applications of the present invention have been illustrated and described, it is to be understood that the invention is not limited to the precise configuration and components disclosed herein. Various modifications, changes, and variations apparent to those of skill in the art may be made in the arrangement, operation, and details of the methods and systems of the present invention disclosed herein without departing from the spirit and scope of the present invention.

What is claimed is:

1. A method for reducing latency in a network data stream comprising:

for each of a plurality of data fragments:
encoding a data fragment into an encoded packet comprising a plurality of codewords, each codeword comprising a set of data bytes from the data fragment and at least one error-correction byte derived from the set of data bytes;
inputting each of the plurality of codewords of the encoded packet into a separate cross-interleaver; and
concatenating a plurality of interleaved codewords output by the separate cross-interleavers into an interleaved packet to be sent over a network.

2. The method of claim 1, further comprising:
generating a compression key indicating which byte or bytes of each interleaved codeword represents padding; and
removing any padding bytes from the interleaved codewords to create a compressed packet.

3. The method of claim 2, wherein each bit of the compression key corresponds to a byte of the interleaved codewords and indicates whether the byte contains data or padding.

4. The method of claim 3, wherein generating comprises:
shifting the bits of the compression key in response to either an encoded packet or a padding packet being input into the plurality of cross-interleavers; and
incrementing the compression key in response to an encoded packet being input into the plurality of cross-interleavers.

5. The method of claim 2, further comprising encapsulating the compressed packet within a network packet.

6. The method of claim 5, wherein encapsulating comprises storing the compression key within the network packet.

7. The method of claim 5, wherein encapsulating comprises storing the compression key within a header of the network packet.

8. The method of claim 1, further comprising inputting a set of padding bytes into the plurality of cross-interleavers in response to a next encoded packet not being ready to be input.

9. The method of claim 1, wherein a first set of codewords are a fraction of the size of a second set of codewords in the encoded packet.

10. The method of claim 1, further comprising segmenting an application packet into the plurality of uniform-length data fragments.

11. The method of claim 1, wherein the application packet comprises multimedia data.

12. The method of claim 1, wherein encoding comprises generating the at least one error-correction byte for each codeword using XOR coding.

13. A method for reducing latency in a network data stream comprising:
for each of a plurality of packets received through a network:
extracting an interleaved packet from a network packet, the interleaved packet comprising a plurality of interleaved codewords;
inputting each of the plurality of interleaved codewords into a separate cross-deinterleaver;
concatenating a plurality of deinterleaved codewords output by the separate cross-deinterleavers into an encoded packet, each of the deinterleaved codewords comprising a set of data bytes and at least one error-correction byte derived from the set of data bytes.

14. The method of claim 13, further comprising:
prior to inputting the plurality of interleaved codewords:
obtaining a compression key from a network packet, the compression key indicating where to insert at least one padding byte within each of the interleaved codewords; and
inserting at least one padding byte within each of the interleaved codewords as indicated by the compression key.

15. The method of claim 14, wherein obtaining comprises extracting the compression key from a header of the network packet.

16. The method of claim 14, wherein each bit of the compression key corresponds to a byte of the interleaved codewords and indicates whether the byte is to contain data or padding.

17. The method of claim 13, further comprising removing the at least one error-correction byte from the deinterleaved codewords of the deinterleaved packet to recover a data fragment of an application packet.

18. The method of claim 17, further comprising assembling a plurality of decoded data fragments into an application packet.

19. A method for reducing latency in a network data stream comprising:
segmenting an application packet into a plurality of data fragments;
for each of the plurality of data fragments:
encoding a data fragment into an encoded packet comprising a plurality of codewords, each codeword comprising a set of data bytes from the data fragment and at least one error-correction byte derived from the set of data bytes;
inputting each of the plurality of codewords of the encoded packet into a separate cross-interleaver;
concatenating a plurality of interleaved codewords output by the separate cross-interleavers into an interleaved packet;
encapsulating the interleaved packet within a network packet; and
transmitting the network packet through a network; and
for each network packet received through the network:
extracting an interleaved packet from a network packet;
inputting each of the plurality of interleaved codewords into a separate cross-deinterleaver;
concatenating a plurality of deinterleaved codewords output by the separate cross-deinterleavers into an encoded packet; and
decoding the encoded packet into a data fragment; and
reassembling a plurality of decoded data fragments into the application packet.

20. The method of claim 19, further comprising:
prior to encapsulating the interleaved packet within a network packet:
generating a compression key indicating which byte or bytes of each interleaved codeword of the interleaved packet represents padding; and
removing any padding bytes from the interleaved codewords of the interleaved packet; and
prior to inputting each of the plurality of interleaved codewords into separate cross-deinterleavers:
extracting the compression key from a network packet, the compression key indicating where to insert at least one padding byte within each of the interleaved codewords; and
inserting at least one padding byte within each of the interleaved codewords as indicated by the compression key.

21. A system for reducing latency in a network data stream comprising:
an encoder that, if executed, causes the encoding of each of a plurality of data fragment into an encoded packet comprising a plurality of codewords, each codeword comprising a set of data bytes from the data fragment and at least one error-correction byte derived from the set of data bytes;
a plurality of cross-interleavers, each cross-interleaver to receive as input one of the plurality of codewords of the encoded packet; and
a concatenator to concatenate a plurality of interleaved codewords output by the plurality of cross-interleavers into an interleaved packet to be sent over a network.

22. The system of claim 21, further comprising:
a compression key generator to generate a compression key indicating which byte or bytes of each interleaved codeword represents padding; and
a packet compressor to remove any padding bytes from the interleaved codewords to create a compressed packet.

23. The system of claim 22, wherein each bit of the compression key represents a corresponding byte of the interleaved codewords and indicates whether the byte contains data or padding.

24. The system of claim 23, wherein the compression key generator is to shift the bits of the compression key in response to either an encoded packet or a padding packet being input into the plurality of cross-interleavers; and wherein the compression key generator is further to increment the compression key in response to an encoded packet being input into the plurality of cross-interleavers.

25. The system of claim 22, further comprising a frame encapsulator to encapsulate the compressed packet within a network packet.

26. The system of claim 25, wherein the frame encapsulator is to store the compression key within the network packet.

27. The system of claim 25, wherein the frame encapsulator is to store the compression key within a header of the network packet.

28. The system of claim 21, further comprising a data flow regulator to input a set of padding bytes into the plurality of cross-interleavers in response to a next encoded packet not being ready to be input.

29. The system of claim 21, wherein a first set of codewords are a fraction of the size of a second set of codewords in the encoded packet.

30. The system of claim 21, further comprising a segmenter to segment an application packet into the plurality of uniform-length data fragments.

31. The system of claim 21, wherein the application packet comprises multimedia data.

32. The system of claim 21, wherein the encoder is to generate the at least one error-correction byte for each codeword using XOR coding.

33. A system for reducing latency in a network data stream comprising:
   a packet receiver to receive a plurality of network packets, each network packet comprising an interleaved packet including a plurality of interleaved codewords;
   a plurality of cross-deinterleavers to receive as input each of the plurality of interleaved codewords; and
   a concatenator to concatenate a plurality of deinterleaved codewords output by the plurality of cross-deinterleavers into an encoded packet, each of the deinterleaved codewords comprising a set of data bytes and at least one error-correction byte derived from the set of data bytes.

34. The system of claim 33, further comprising a packet decompressor to obtain a compression key from a network packet, the compression key indicating where to insert at least one padding byte within each of the interleaved codewords; wherein the packet decompressor is further to insert at least one padding byte within each of the interleaved codewords as indicated by the compression key.

35. The system of claim 34, wherein the packet decompressor is to extract the compression key from a header of the network packet.

36. The system of claim 34, wherein each bit of the compression key represents a corresponding byte of the interleaved codewords and indicates whether the byte is to contain data or padding.

37. The system of claim 33, further comprising a decoder to remove the at least one error-correction byte from the deinterleaved codewords of the deinterleaved packet to recover a data fragment of an application packet.

38. The system of claim 37, further comprising a reassembler to join a plurality of decoded data fragments into an application packet.

39. A system for reducing latency in a network data stream comprising:
   a segmenter to segment an application packet into a plurality of data fragments;
   an encoder to encode each of the plurality of data fragments into an encoded packet comprising a plurality of codewords, each codeword comprising a set of data bytes from the data fragment and at least one error-correction byte derived from the set of data bytes;
   a plurality of cross-interleavers, each cross-interleaver to receive as input one of the plurality of codewords of the encoded packet;
   a concatenator to concatenate a plurality of interleaved codewords output by the plurality of cross-interleavers into an interleaved packet to be sent over a network;
   a frame encapsulator to encapsulate the interleaved packet within a network packet for transmission through a network;
   a packet receiver to receive a plurality of network packets through the network, each network packet comprising an interleaved packet including a plurality of interleaved codewords;
   a plurality of cross-deinterleavers to receive as input each of the plurality of interleaved codewords;
   a concatenator to concatenate a plurality of deinterleaved codewords output by the plurality of cross-deinterleavers into an encoded packet, each of the deinterleaved codewords comprising a set of data bytes and at least one error-correction byte derived from the set of data bytes;
   a decoder to decode the encoded packet into a data fragment; and
   a reassembler to join a plurality of decoded data fragments into the application packet.

40. A computer program product comprising program code for performing a method for reducing latency in a network data stream, the computer program product comprising:
   program code that, if executed, causes the encoding of each of a plurality of data fragments into an encoded packet comprising a plurality of codewords, each codeword comprising a set of data bytes from the data fragment and at least one error-correction byte derived from the set of data bytes;
   program code that, if executed, causes the input of each of the plurality of codewords of the encoded packet into a separate cross-interleaver; and
   program code that, if executed, causes the concatenation of a plurality of interleaved codewords output by the separate cross-interleavers into an interleaved packet to be sent over a network.

41. The computer program product of claim 40, further comprising:
   program code to generate a compression key indicating which byte or bytes of each interleaved codeword represents padding; and
   program code to remove any padding bytes from the interleaved codewords to create a compressed packet.

42. The computer program product of claim 41, further comprising:
   program code to encapsulate the compressed packet within a network packet; and
   program code to store the compression key within the network packet.

* * * * *